(12) United States Patent
Bassot et al.

(10) Patent No.: US 8,387,467 B2
(45) Date of Patent: Mar. 5, 2013

(54) METHOD FOR TESTING THE COATING OF A VANE BASE

(75) Inventors: Alain Bassot, Bois le Roi (FR); Laurent Dudon, Viry-Chatillon (FR); Anne-Claire Perriau, Vaux le Penil (FR)

(73) Assignee: SNECMA, Paris (FR)

( * ) Notice: Subject to any disclaimer, the term of this patent is extended or adjusted under 35 U.S.C. 154(b) by 206 days.

(21) Appl. No.: 12/919,268

(22) PCT Filed: Feb. 25, 2009

(86) PCT No.: PCT/FR2009/050295
§ 371 (c)(1),
(2), (4) Date: Feb. 23, 2011

(87) PCT Pub. No.: WO2009/112756
PCT Pub. Date: Sep. 17, 2009

(65) Prior Publication Data
US 2011/0138926 A1    Jun. 16, 2011

(30) Foreign Application Priority Data
Feb. 25, 2008   (FR) .................................. 08 51181

(51) Int. Cl.
| | |
|---|---|
| G01B 5/30 | (2006.01) |
| G01B 17/00 | (2006.01) |
| G01L 5/04 | (2006.01) |
| G01D 7/00 | (2006.01) |
| G01N 1/00 | (2006.01) |
| G01N 11/00 | (2006.01) |
| A61C 19/00 | (2006.01) |
| A61C 19/04 | (2006.01) |
| C23C 16/52 | (2006.01) |
| B05D 1/40 | (2006.01) |

(52) U.S. Cl. ...... 73/760; 73/150 R; 73/158; 73/862.046; 73/863; 73/54.22; 433/32; 433/68; 427/8; 427/478

(58) Field of Classification Search ........................ None
See application file for complete search history.

(56) References Cited

U.S. PATENT DOCUMENTS
3,802,255 A     4/1974   Struthers et al.
5,129,253 A *   7/1992   Austin et al. ............... 72/370.07
(Continued)

FOREIGN PATENT DOCUMENTS
EP     1 598 655      11/2005
EP     1 705 261      9/2006

OTHER PUBLICATIONS

U.S. Appl. No. 12/919,017, filed Aug. 24, 2010, Bassot, et al.

*Primary Examiner* — David Gray
*Assistant Examiner* — Naeem M Jahangir
(74) *Attorney, Agent, or Firm* — Oblon, Spivak, McClelland, Maier & Neustadt, L.L.P.

(57) ABSTRACT

A method for testing a coating for blade roots, includes: providing a disk test piece including at least one bearing surface and a blade test piece including at least one bearing surface coated with the coating to be tested, the blade test piece including two test piece halves adapted to be engaged on either side of the disk test piece, and subjecting the blade test piece engaged with the disk test piece to tensile cycles during which the test pieces undergo tensile stress with respect to each other in a tensile direction, the tensile strain being transmitted via the bearing surfaces contacting the blade test piece and the disk test piece. The method allows for very faithful reproduction of the behavior and ageing of the coating and thus allows for accurate evaluation of the quality of the coatings.

15 Claims, 2 Drawing Sheets

U.S. PATENT DOCUMENTS

| | | |
|---|---|---|
| 6,250,166 B1 | 6/2001 | Dingwell et al. |
| 6,910,866 B2 | 6/2005 | Bassot et al. |
| 7,108,484 B2 | 9/2006 | Thenaisie et al. |
| 7,144,602 B2 | 12/2006 | Bengtsson et al. |
| 2002/0194733 A1* | 12/2002 | Surace et al. ............ 29/889.1 |
| 2005/0050942 A1* | 3/2005 | Schmitt .......................... 73/7 |
| 2005/0084379 A1* | 4/2005 | Schreiber ..................... 416/230 |
| 2005/0252304 A1 | 11/2005 | Woodward et al. |
| 2005/0254951 A1* | 11/2005 | Thenaisie et al. ........ 416/219 R |
| 2006/0216429 A1 | 9/2006 | Bengtsson et al. |
| 2008/0026160 A1* | 1/2008 | Taylor et al. .................. 427/454 |
| 2008/0299170 A1* | 12/2008 | Lambert et al. ............... 424/423 |
| 2009/0252968 A1* | 10/2009 | Werger ......................... 428/408 |
| 2011/0214497 A1* | 9/2011 | Sellars et al. ............... 73/150 A |
| 2012/0114929 A1* | 5/2012 | Xie et al. ..................... 428/312.8 |
| 2012/0152007 A1* | 6/2012 | Holmes et al. ............. 73/112.01 |
| 2012/0269641 A1* | 10/2012 | Chessick ................... 416/223 R |

\* cited by examiner

METHOD FOR TESTING THE COATING OF A VANE BASE

This invention relates to the field of quality control of antifriction coatings for turbomachine blade roots. More precisely, the invention relates to a method for testing a coating intended to coat a blade root for turbomachines.

Blades, and in particular fan blades in aeronautical turbomachines (turbo-reactors or turboprops), are extremely stressed mechanical parts. For this reason, the blade root, which is the holding portion of the blade, is a particularly critical portion of the blade. The blade root comprises contact or bearing surfaces, which in operation are subjected to stresses and high temperatures. In order to reduce the stresses, and namely the shearing stresses, which are applied to the bearing surfaces of the blade roots, antifriction coatings are used in a known manner. These so-called antifretting coatings can be deposited namely by thermal projection. They may be multi-layered. The quality of the antifriction coating is essential, as a main type of failure of the blades is related to the disintegration (through chipping, cracking, crumbling, or wear) of the coating.

Typically, the durability of the coating of a blade root is related to the number of cycles (the so-called 'engine cycles') undergone by the blade. Such a cycle is in fact the set of stresses to which the blade is subjected during a complete operating phase of the turbomachine (in flight, for a turbo-reactor mounted on an airplane), i.e. from start to stop. Thus, in particular for an airplane, a cycle comprises a take-off and a landing.

The durability of the coating expressed as a number of cycles may be related to a business agreement, meet specifications, or be specified by an engineering office. The blade root coating must remain operational during the whole lifetime of the blade, as usually no intervention is scheduled for the coating of a blade root throughout operation thereof.

In order to ensure quality of this coating, and the interface thereof with the material of the blade itself, in a known manner micrographic coating tests are performed, which generally consist in sectioning the coating and the blade root and examining the aspect of this section under the microscope. Such a test allows to check the internal structure and thickness of the coating, and to some degree, the quality of the interface thereof with the material of the blade root as such. It is also known to test the quality of the coating through standard hardness tests, or through tensile or shear adhesion tests.

However, it appeared that the various tests prove to be insufficient for distinguishing high quality coatings from just acceptable quality coatings, and for forming a precise opinion about the durability and mechanical aspect in use of the coating deposited on the blade root: In other words, the present tests do not allow to establish a difference of quality between the various coatings as long as they withstand a number of cycles in a satisfactory manner.

The aim of the invention is to propose a method for testing a coating for blade roots, which proves to be more differentiating test prior tests as to the quality of the coatings, and allows to obtain highly correlated results with the actual assessments of stability in time of the blade root coatings, as obtained throughout the lifetime of a blade, i.e. commonly from 10,000 to 15,000 cycles.

This aim is achieved by means of a method comprising the following steps:
providing a so-called disk test piece comprising at least one bearing surface, and another so-called blade test piece comprising at least one bearing surface coated with said coating to be tested, the blade test piece being composed of two test piece halves adapted to be engaged on either side of the disk test piece,
subjecting the blade test piece engaged with the disk test piece to tensile cycles during which the test pieces undergo tensile stress with respect to each other in a tensile direction, with tensile strain being transmitted via the bearing surfaces contacting the blade test piece and the disk test piece;
evaluating said coating depending on a predetermined evaluation criterion.

The principle of the test thus defined is basically different from previously known tests. Indeed, instead of being based on the examination of new blade roots, it consists in subjecting blade roots, and more precisely the bearing surfaces thereof, to fatigue tests representing the stresses which they will undergo during the lifetime of the blade. Advantageously, the method does not require the use of blades, but merely the use of two test pieces, the blade test piece of which in particular having a bearing surface coated with the coating to be tested. It should be noted that it is furthermore perfectly possible for the blade test piece to have not only one but several bearing surfaces, the disk test piece then comprising one bearing surface for each of the bearing surfaces of the blade test piece.

The objective of the test of the blade coating can be for instance to generally test a new coating, or effectively validate the quality of the coating applied to a series of blades to be put into operation. According to the target objective, the test pieces used, and the test conditions (number of cycles, maximum force applied during the same) can be more or less representative of the actual stresses to which the coating is subjected during operation of the blade root. Thus, typically, the number of tensile cycles and the maximum tensile force applied to the test pieces are determined for a given coating depending on the maximum admissible pressure on the bearing surfaces of the blade root and the number of engine cycles during the lifetime of the blade.

Furthermore, during tensile cycles, displacements occur depending on the transmitted strains. A tensile cycle is characterized by the variation curve of the tensile force as a function of time. In practice, tensile force is increased from an initial zero, or at least low value (with respect to the maximum value) up to the maximum value, then returning to the initial value. The initial value and the maximum value, independently one and/or the other, may be maintained for some time. Furthermore, other tensile cycle profiles can be envisaged, depending on how the different operating phases of the turbomachine are to be simulated. The run-up rate parameter, i.e. the increase of the tensile force per unit of time, can also be adjusted.

Typically, the blade test piece is subjected to 3,000 to 15,000 tensile cycles, with tensile forces variable between 15,000 and 30,000 daN.

The evaluation of the test pieces can be done either during the tensile cycles (using for instance sensors mounted on the test machine, like cameras and/or ultrasound sensors), or at the end of the tensile cycles, once the test pieces have been removed.

According to one embodiment, during the evaluation step of the method, the blade test piece is examined so as to determine if it exhibits chipping or crumbling on its bearing surface(s).

The advantage of the inventive method is that it provides results which are highly representative of the behavior and ageing of the coatings of the real blade roots.

In a known manner, fastening a blade to a rotor disk is done in general by means of a mortise-and-tenon coupling forming an attachment. This attachment is composed of a tenon made at one radially interior end of the blade, which is secured in a mortise provided on the periphery of the rotor disk. The blade roots on the one hand, the rotor disk bosses or tenons formed between the rotor disk mortises on the other hand, are thus respectively complementary dovetail shapes, arranged radially in the opposite direction so as to ensure mutual fastening between the blades and the rotor disk.

In an impeller, the blades are evenly attached on the outer periphery of the rotor disk, which thus comprises as many fastening cells as there are blades to be fastened.

The attachments of the blades to the rotor disk form a pattern repeated in the circumferential direction and which can be defined e.g. by the blade root and the corresponding mortise of the rotor disk, or by the dovetail tenon (or dovetail) of the rotor disk and the two blade root halves enclosing the same in the impeller.

Thus, it is understood that the principle of the inventive method precisely consists in reproducing the cyclic stresses undergone by the pattern, i.e. the stresses of the dovetail tenon of the rotor disk held by two blade root halves.

The blade test piece is composed of two test piece halves adapted to be engaged on either side of the disk test piece, or counter test piece, reproducing a unitary pattern. The symmetrical arrangement of the test piece halves around the counter test piece allows for lateral strains applied thereto during tensile cycles to be symmetrical in the opposite direction, and thus to cancel each other. Thereby, the method advantageously does not require any mechanical means adapted to bear lateral strains which the counter test piece would undergo during tensile cycles. Furthermore, in case the blade root has bearing surfaces on both faces thereof, which are not symmetrical, this arrangement with two test piece halves enclosing one counter test piece allows for the test pieces to have bearing surfaces representing the two contact faces of the blade root. As these bearing surfaces are tested during the same test, the latter allows for simultaneous testing and checking of the behavior of the coating for both faces of the blade root.

Furthermore, the method allows to obtain results which are highly representative of reality. Indeed, the arrangement of the test pieces corresponds to their respective positions in a turbomachine: The two test piece halves representing the two halves of a blade root enclose on either side and retain a counter test piece representing a tenon of the rotor disk. It has been found that in this arrangement, excellent representativeness of the results is obtained.

According to one embodiment, the bearing surface(s) of the blade test piece and the disk test piece have complementary shapes and extend in a sloped direction with respect to the tensile direction, so that the contact between these bearing surfaces represents that of a blade root with a turbomachine rotor disk tenon. The sloped shape of the bearing surfaces converts the radial tensile strain into strains in the transverse or circumferential direction.

Advantageously, the bearing surfaces of the blade test piece and/or the disk test piece form an angle of about 45° with respect to the tensile direction. More generally speaking, this angle may vary between 30 and 60°.

According to one embodiment, the blade test piece has close to the bearing surface(s) thereof a shape representing a turbomachine blade root, with the tensile axis being the radial axis of said blade root. This shape for the blade test piece allows to test the coating under the conditions which are most representative of the operating conditions thereof. In particular, the blade test piece can have a behavior and mechanical deformations representing those of a blade root or the blade root for which the coating is meant.

According to one embodiment, the disk test piece has close to the bearing surface(s) thereof a shape representing a turbomachine rotor disk tenon. This shape involves the portion of the test piece with which it is located on the side of the blade test piece.

The respective bearing surfaces of the test pieces thus respectively represent bearing surfaces of the blade root and the corresponding tenon of the rotor disk. Furthermore, so as to allow for a faithful representation of the behavior of the attachment, i.e. of the blade root with respect to the tenons of the rotor disk, usually a blade test piece is made from the same material as the blade root; i.e. typically from a titanium base alloy for the high and low pressure compressor, from a nickel base alloy for the engine portions the operating temperature of which will exceed 500° C. For the same reasons, it is also possible to choose a material identical to that of the rotor disk for the disk test piece, i.e. also from a titanium or nickel base alloy.

Testing is done preferably by means of a tensile test machine. This machine comprises on a frame of first and second holding means respectively holding a first and a second one of the test pieces. Throughout the test, these holding means allow to maintain the test pieces in the required position, which is the engaged position of both test pieces in which the respective bearing surfaces thereof coincide and make contact. This position preferably reproduces the respective positions of the blade root and the rotor disk in operation.

The machine further comprises tensile means imposing alternating displacements of one holding system with respect to the other, in a tensile direction. The holding systems are then subjected to tensile motions relatively to each other, so as to subject the bearing surfaces, and namely the bearing surfaces of the blade test piece, to stresses representing those experienced by the blade root in operation. Displacements in the tensile direction are usually measured and recorded by a displacement measuring system, such as a comparator.

At the end of the tensile cycles, the coating of the bearing surfaces of the blade test piece is evaluated. This evaluation can be done in particular by visual (i.e. macrographic) or micrographic inspection; additional inspections, such as bonding, shock resistance, and other testing, are also possible in this phase. For this inspection, an evaluation criterion for the blade root coating has to be defined, depending on which the decision to accept or reject the coating will be made. The criterion is generally the absence of disintegration through chipping or crumbling of the coating, throughout the bearing surface(s) of the blade. For instance, a visual reference system showing maximum admissible chips (in number, dimension) is used. Observing a maximum size for the chips can be checked also by geometrical measurements.

Finally, it should be noted that preferably the test method is not implemented once, for a given coating; on the contrary, in general the evaluation test of the coating consists of a series of tests (for instance three), so as to increase the reliability of the results: The results can thus be calculated by means of statistical methods, which allows for variation thereof to be reduced.

In this case, the method for testing the blade root coating comprises the following steps:
 running the previously defined test on one or more test piece pairs, each test piece pair comprising one blade test piece, the bearing surface(s) of which are coated with the coating to be tested, and one disk test piece; and analyzing the results obtained by means of statistical methods, so as to qualify the quality of the blade coating.

The evaluation criterion of the blades may for instance be the following: the blades qualify and are accepted if none of them exhibits chipping after 13,500 cycles at a maximum tensile force of 20,000 daN. It is also possible to accept a given percentage of defects.

Also, the efficiency of the tests performed can be further increased by observing the evolution of the chipping of the blade test piece during the tensile cycles (and not at the end). Thereby, unsatisfactory coatings can be detected earlier.

Again according to this principle, in a variant of the inventive method, the evaluation of the test pieces is done during the tensile cycles, and the number of these cycles is not fixed in advance. In this case, the cycles are stopped as soon as a stopping criterion has been reached, such as for instance the presence of chipping in the coating of the bearing surfaces of the blade test piece.

According to another embodiment of the invention, the method further comprises the following step: fixing in advance the parameters of the tensile cycles.

The evaluation of the coating is then performed after a predetermined number of the tensile cycles. Thus, according to the method, at the beginning, the parameters of the tensile cycles are fixed, and an evaluation criterion is chosen; the test pieces are subjected to the tensile cycles thus scheduled; and at the end of the cycles, in general after the test pieces have been removed, they are evaluated with reference to the evaluation criterion.

The parameters of the tensile cycles are usually the number of cycles, the maximum force applied during the cycle, or the rate of increase or decrease of the tensile force as a function of time, temperature, or the like. They are fixed before the beginning of the test, just like the number of cycles, depending on the coating and the blade to be evaluated, and the operating modes of the turbomachine to be simulated.

It should be noted in particular that for testing the quality of a blade root coating using the inventive method, it is possible to choose to increase the number of cycles by reducing the maximum tensile force during the cycle, or vice versa. Indeed, it has been found for blade root coatings that while the parameters stay in a range of reasonable values for the blade root (e.g. excluding pressure which would exceed mechanical resistance of the material of the blade root itself), it is substantially the same for testing the quality of the coating in a batch of blade test pieces to perform a small number of cycles, with high tensile force, or a greater number of cycles, with lower tensile force. E.g., in a substantially equivalent manner, it is possible to test a coating, which coats the test pieces, by subjecting the same either to 15,000 tensile cycles at a maximum force of 15,000 daN, or 6,000 tensile cycles at a maximum force of 19,000 daN.

According to one embodiment, during the tensile cycles, resilient return means will limit the lateral opening of the test pieces, which occurs in response to the opening force applied by the test pieces to each other under the effect of tension. Lateral opening (in the direction perpendicular to the tensile direction) of the two test pieces reproduces the fact that in the turbomachine, during operation, the rotor disk tenons and the blade roots will deform, and in particular so in case the test pieces comprise bearing surfaces arranged in an sloped direction with respect to the tensile direction. Due to this possibility of limited lateral opening of the test pieces, thanks to the resilient return means, the representativeness of the results obtained by means of the method is increased.

According to a development of the preceding embodiment, with the aim of tracking the behavior of the test pieces during tensile cycles, during the tensile cycles, lateral opening of the test pieces is measured. This parameter allows to make sure that the relative positions of the test pieces with respect to each other will still be representative of the positions in which the coating is to be tested.

The invention will be better understood and the advantages thereof will be more apparent from reading the following detailed description of embodiments represented by way of example and not being restrictive. The description refers to the appended drawings, in which:

FIGS. 1 and 2 are partial sectional views of test pieces 22, 32 used for implementing the inventive method, shown as being mounted in a test machine.

Figure 1:
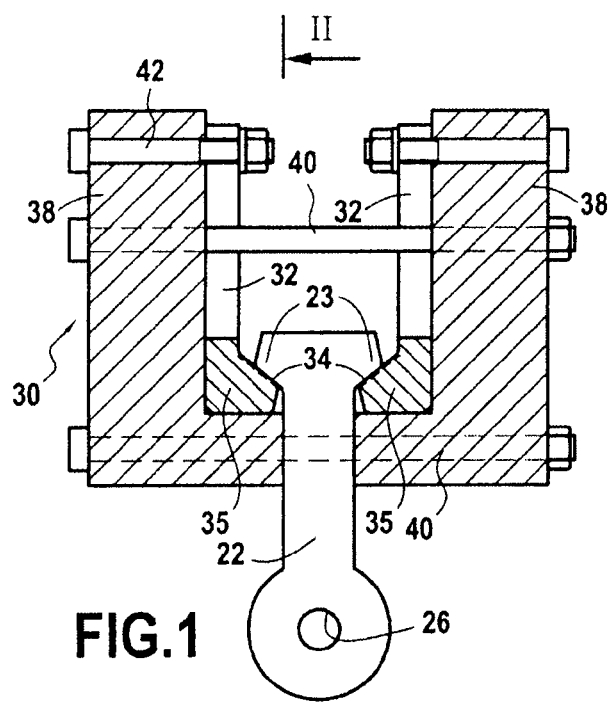
FIGS. 1 and 2 are respectively front and side partial sectional views of test pieces used for implementing the inventive method, represented in a test machine.

According to the method, for testing a blade root coating, a first step consists in making test pieces which will be employed and used up in testing. Such test pieces are made in pairs, each pair comprising one so-called blade test piece 32, and one so-called disk test piece 22.

The disk test piece 22 is also designated as a counter test piece. At one end (the upper end in FIG. 1), it has a relatively symmetrical bulb, the sides 23 of which project in cantilever fashion on either side of the spindle thereof. At the other end, it further has fastening means, enabling it to be fastened to the test machine by means of first holding means used to retain the disk test piece during tensile testing. Herein, such means are a bore, provided for a fastening spindle 26 of the test machine to go through.

The blade test piece in turn is composed of two test piece halves 32, positioned around the disk test piece 22. The test piece halves 32 comprise opposite contact surfaces, or bearing surfaces, which in the test position make contact with corresponding bearing surfaces of the test piece 22. The bearing surfaces 34 of the test piece halves 32 are located on the inclined top faces of bulges 35 formed on the base of the test piece halves 32. The bearing surfaces 34 of the test piece halves 32 are contact surfaces which are comparable with the bearing surfaces of a blade root, with the bearing surfaces of the test piece being in turn comparable with the bearing surfaces of the dovetail tenon of the rotor disk.

Figure 2:
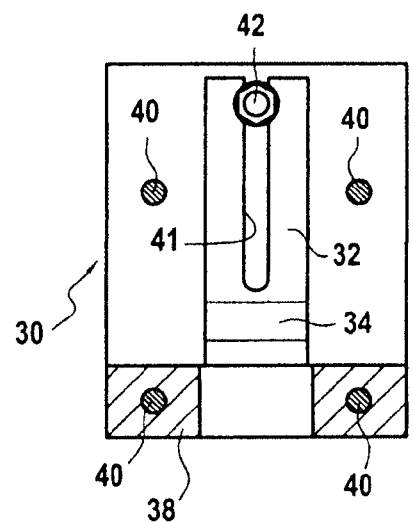

In the test machine enabling implementation of the inventive method, as shown in FIGS. 1 and 2, the test piece halves 32 are held by a holding system 30. It is used to hold the two test piece halves 32, and more precisely hold the bearing surfaces 34 of the same, opposite the corresponding bearing surfaces of the counter test piece 22, throughout testing. The holding system 30 comprises parallel posts 38, and resilient return means 40 of the posts 38 with respect to each other. In this example, these resilient return means are four screws 40, which solidly hold the test piece halves in place around the counter test piece 22. The test piece halves 32 are secured to the posts 38 by screws 42, going through elongated holes 41 made in the test piece halves, in portions thereof remote from the bulges 35 thereof.

It should further be noted that the method can also be implemented with two posts 38 rigidly fastened to each other or even forming a single part only, but advantageously, the posts 38 are independent portions within the holding system 30.

Figure 3:
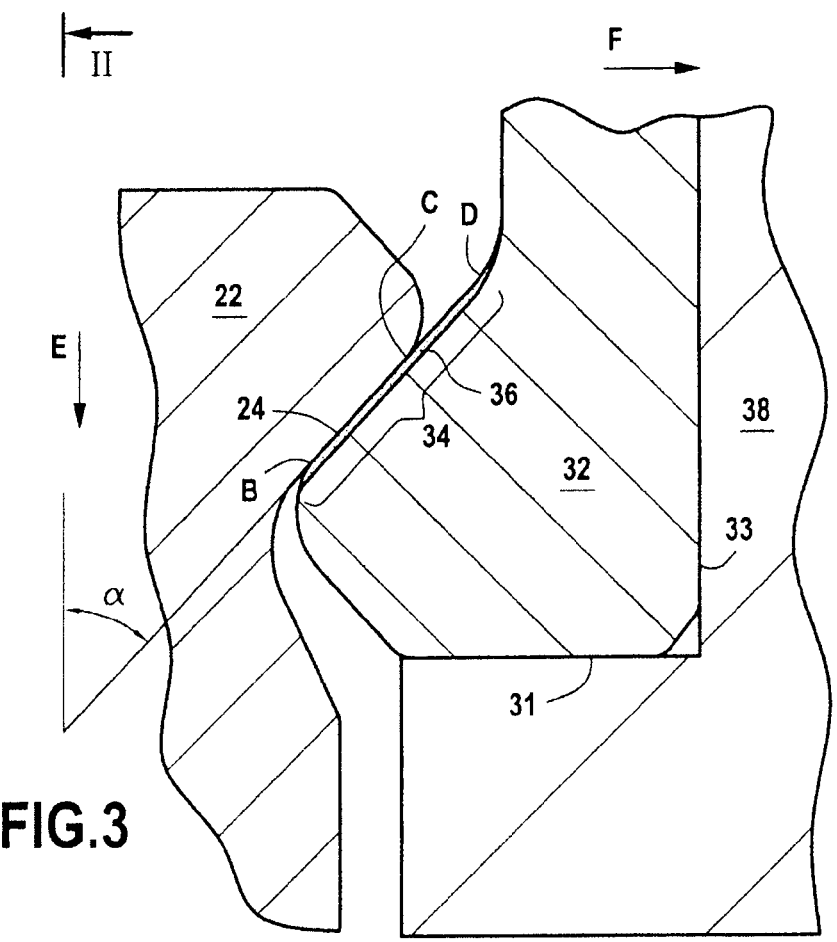
FIG. 3 is a partial axial sectional view of these test pieces in the area of the bearing surfaces thereof.

FIG. 3 shows more in detail the shapes making contact with the test piece 22 and one test piece half 32. Test piece half 32 is represented as resting on the post 38, with the lower 31 and rear 33 faces thereof. The test piece half 32 comprises a bearing surface 34 extending between point B and point D. On this bearing surface 34, the test piece half 32 is coated with the coating 36 to be tested. This coating is of the same kind and applied according to the same method as the coating used for protecting the bearing surfaces of the blade roots. This coating projects on either side of the contact area 24 which is part of the bearing surface 34. Indeed, in the represented relative position of the test piece half 32 and the counter test piece 22, the contact area 24 only extends over one portion of the bearing surface 34, between points B and C. Of course, during tensile testing, the position of this contact area will vary with respect to the bearing surface 34.

As can be seen in FIG. 3, the bearing surfaces of test piece 22 and test piece half 32 are arranged in a slanted or inclined direction with respect to direction E, which is the tensile direction. This is the inclination to be found where the blade root is fastened to the rotor disk. The angle of inclination a is close to 45°.

The second step of the method consists in subjecting the test pieces to tensile cycles. This operation is performed on a test machine as the one mentioned before, represented in FIG. 4.

This machine 10 comprises a framework 12 generally composed of a mechanically welded frame. This framework 12 supports two holding systems 20 and 30.

The first holding system 20 located in the bottom portion of the machine comprises a fixed column 29 holding the counter test piece 22 in place. The counter test piece 22 comprises a bore through which goes a spindle 26 of the first holding system, by means of which the counter test piece 22 is maintained, no matter which tensile stresses it will receive.

The second holding system 30 is used to hold the two test piece halves 32 in place. This holding system 30 comprises a mobile beam 39 set into a straight alternating translatory motion in the vertical direction along the double arrow A, by a linear actuator 14 or any other equivalent actuating means. This beam 39 is guided in its alternating vertical translatory motion by slide bars 16. The holding system 30 further comprises means for rigidly connecting the test piece halves 32 with respect to the beam 39, which namely comprise the above-mentioned posts 38.

The characteristics of the linear actuator 14 are chosen so that the latter can impart to the second holding system 30 with respect to the first one 20 vertical translatory motions representing those performed by a blade, and more precisely by the blade root, with respect to the rotor disk during the operation of the turbomachine to which the blade belongs. Such motions are due to significant centrifugal forces received by the blades during rotation of the engine. Such centrifugal forces are comparable with radial tension on the blade.

Figure 4:
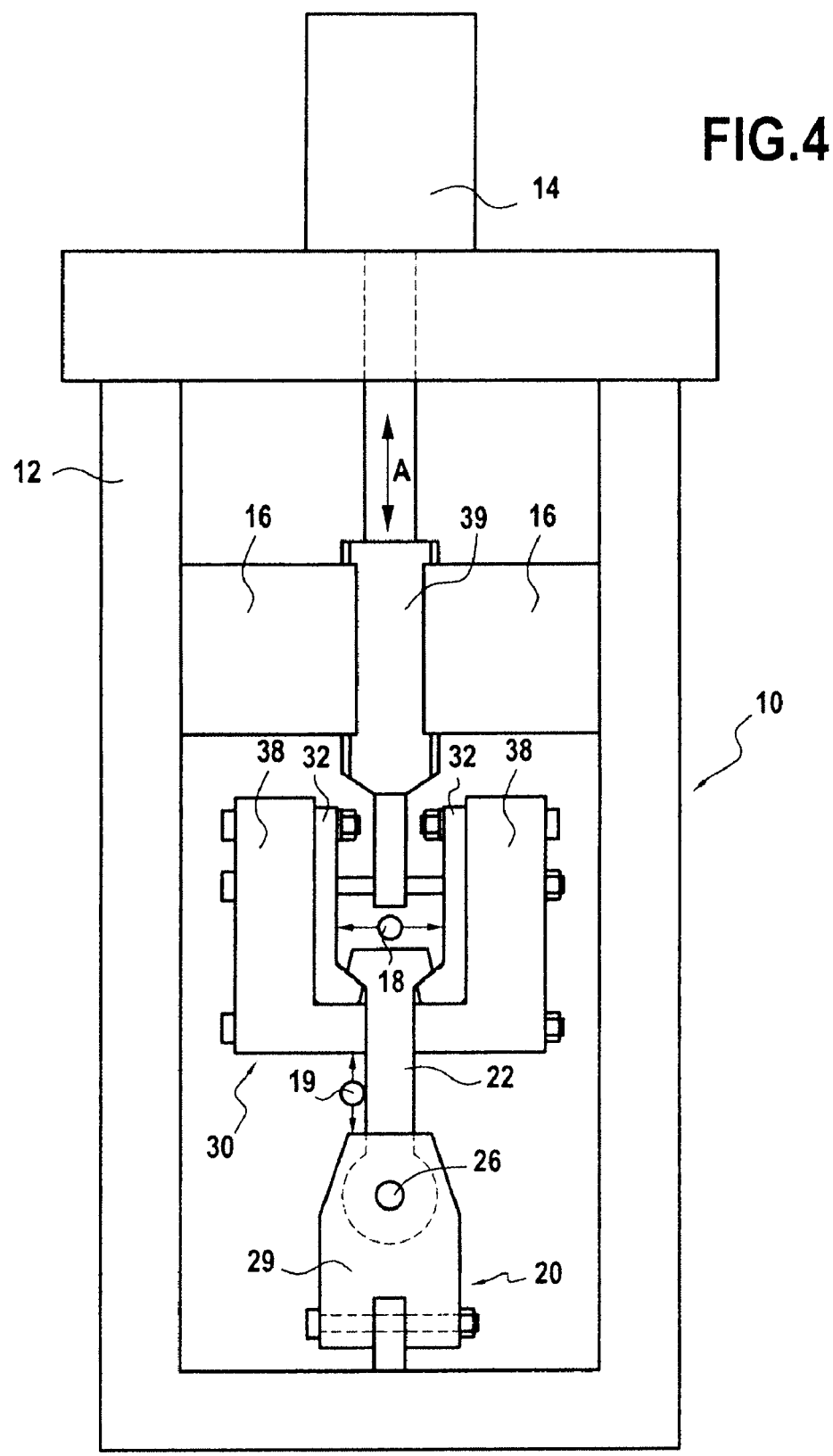
FIG. 4 is an axial sectional view of a test machine allowing for the inventive method to be implemented.

The principle of the tensile cycles is to subject the test pieces to stress cycles in a so-called tensile direction, with the test pieces being arranged so that the tensile strains are transmitted via their opposite bearing surfaces, as can be seen in the various figures. The respective bearing surfaces of the test piece halves and the counter test piece are thus forced and pressed into contact with each other, which allows for testing, putting to test, the coating of the blade test piece (herein the two test piece halves). In the machine of FIG. 4, the stresses are applied to the test piece halves 32, with test piece 22 (i.e. the counter test piece) being fixed. The inverted configuration is also possible.

In the machine 10, when test piece 22 is subjected to tensile stress (arrow E), the bearing surface thereof makes contact with the bearing surface 34 of the test piece half. Due to the angle of inclination a, under the effect of the contact, the axial force in the tensile direction E applied to test piece 22 is converted into a transverse force in the direction of arrow F, applied to the test piece half 32. In order to withstand such opening forces, the posts 38 are connected by screws 40 preventing them from opening up. Such screws have some calculated elasticity, which enables them to stretch slightly in response to such forces, and thus reproduce the deformation of the blade root and the rotor disk tenons under the effect of the rotation of the rotor.

This possibility of lateral displacement of the two posts 38, in the circumferential direction with respect to the blade root (i.e. perpendicularly to the tensile direction and the bearing surfaces of the blade root) allows for better reproduction of the holding conditions of the blade in operation.

In order to check proper operation of the tensile cycles which the blade roots will undergo, the machine further comprises means for measuring the movements of the test piece halves during testing. This measurement allows to ensure proper operation and correct positioning of the various parts during testing. It may comprise a first measuring system 19 of displacements along the tensile axis, and a second measuring system 18 of the lateral opening of the test piece halves 32.

As an example, a real procedure for testing a blade root coating according to the inventive method using the machine of FIG. 4 will now be described in detail.

First of all, it should be noted that for testing a pair of test pieces, the procedure is the following:
preparing a pair of test pieces composed of two blade test piece halves and one disk test piece;
subjecting this pair of test pieces to 10,000 tensile cycles, the tensile force varying according to the same profile as a function of time during each of the tensile cycles; and
then examining the condition of the bearing surfaces of the blade test piece halves, so as to determine if this condition is acceptable or not. The result of the test is considered satisfactory for the pair of test pieces if there is no chipping and/or wear down to the material of the test piece as such on the bearing surfaces of the blade test piece halves.

The number of tensile cycles (10,000) and the profile for varying tensile force as a function of time during the tensile cycles are determined in advance depending on the blade for which the coating is intended.

This method for testing a pair of test pieces having been defined, it is now possible to specify how to qualify the blade coating:

For qualifying the blade coating, according to the preceding method, three pairs of test pieces are tested.

The coating qualifies if satisfactory results are obtained for at least two out of three pairs of test pieces.

The invention claimed is:

1. A method for testing a coating for blade roots, comprising:
providing a disk test piece comprising at least one bearing surface, and a blade test piece comprising at least one bearing surface coated with the coating, the blade test piece including two test piece halves adapted to be engaged on either side of the disk test piece;
subjecting the blade test piece engaged with the disk test piece to tensile cycles during which the test pieces undergo tensile stress with respect to each other in a tensile direction, the tensile strain being transmitted via the bearing surfaces contacting the blade test piece and the disk test piece; and
evaluating the coating depending on a predetermined evaluation criterion.

2. The method according to claim 1, wherein the bearing surfaces of the blade test piece and the disk test piece have complementary shapes and extend in a slanted direction with respect to the tensile direction.

3. The method according to claim 1, wherein during the tensile cycles, through a resilient return means, a lateral opening of the test pieces is limited, which occurs in response to an opening force applied by the test pieces to each other under the effect of tension.

4. The method according to claim 3, wherein during the tensile cycles the lateral opening is measured.

5. The method according to claim 1, wherein the bearing surfaces of the blade test piece and the disk test piece have complementary shapes and extend in a slanted direction with respect to the tensile direction, and during the tensile cycles, through a resilient return means, a lateral opening of the test pieces is limited, which occurs in response to an opening force applied by the test pieces to each other under effect of tension.

6. The method according to claim 5, wherein during the tensile cycles the lateral opening is measured.

7. The method according to claim 1, wherein close to the bearing surface(s) thereof, the blade test piece has a shape representing a turbomachine blade root, with the tensile axis being the radial axis of the blade root.

8. The method according to claim 2, wherein close to the bearing surface(s) thereof, the blade test piece has a shape representing a turbomachine blade root, with the tensile axis being the radial axis of the blade root.

9. The method according to claim 3, wherein close to the bearing surface(s) thereof, the blade test piece has a shape representing a turbomachine blade root, with the tensile axis being the radial axis of the blade root.

10. The method according to claim 4, wherein close to the bearing surface(s) thereof, the blade test piece has a shape representing a turbomachine blade root, with the tensile axis being the radial axis of the blade root.

11. The method according to claim 5, wherein close to the bearing surface(s) thereof, the blade test piece has a shape representing a turbomachine blade root, with the tensile axis being the radial axis of the blade root.

12. The method according to claim 6, wherein close to the bearing surface(s) thereof, the blade test piece has a shape representing a turbomachine blade root, with the tensile axis being the radial axis of the blade root.

13. The method according to claim 1, wherein close to the bearing surface(s) thereof, the disk test piece has a shape representing a turbomachine rotor disk tenon.

14. The method according to claim 1, further comprising:
fixing in advance parameters of the tensile cycles; the evaluation of the coating being performed after a predetermined number of tensile cycles.

15. The method according to claim 1, wherein the evaluation comprises a visual or micrographic inspection.

* * * * *